United States Patent
Tok et al.

(10) Patent No.: US 10,215,630 B2
(45) Date of Patent: Feb. 26, 2019

(54) RAMAN SPECTROSCOPY SYSTEMS AND RAMAN SPECTROSCOPY METHODS

(71) Applicant: EINST Technology Pte Ltd, Singapore (SG)

(72) Inventors: Wee Lee Tok, Singapore (SG); Eddie Khay Ming Tan, Singapore (SG)

(73) Assignee: EINST TECHNOLOGY PTE LTD, Singapore (SG)

( * ) Notice: Subject to any disclaimer, the term of this patent is extended or adjusted under 35 U.S.C. 154(b) by 120 days.

(21) Appl. No.: 14/898,759

(22) PCT Filed: Oct. 24, 2014

(86) PCT No.: PCT/SG2014/000501
§ 371 (c)(1),
(2) Date: Dec. 16, 2015

(87) PCT Pub. No.: WO2016/064339
PCT Pub. Date: Apr. 28, 2016

(65) Prior Publication Data
US 2016/0370228 A1  Dec. 22, 2016

(51) Int. Cl.
*G01J 3/44* (2006.01)
*G01J 3/02* (2006.01)
(Continued)

(52) U.S. Cl.
CPC ............. *G01J 3/0205* (2013.01); *G01J 3/02* (2013.01); *G01J 3/0208* (2013.01); *G01J 3/44* (2013.01);
(Continued)

(58) Field of Classification Search
CPC ........... G01J 3/44; G02B 26/04; G01N 21/65; G01N 2021/4726
See application file for complete search history.

(56) References Cited

U.S. PATENT DOCUMENTS 4,097,751 A * 6/1978 Egan ...................... G01N 21/55
  250/559.01
4,448,529 A * 5/1984 Krause .................. G01J 3/2846
  250/281
(Continued)

FOREIGN PATENT DOCUMENTS

CN  103487146 A  1/2014

OTHER PUBLICATIONS

R.S. Barlow, "Shutter-based line imaging system for single-shot Raman scattering measurements of gradient in mixture fraction" hereafter Barlow, 2000.*
(Continued)

*Primary Examiner* — Maurice Smith
(74) *Attorney, Agent, or Firm* — Viering, Jentschura & Partner mbB (57) ABSTRACT

According to various embodiments, a Raman spectroscopy method is provided for reduction of background fluorescence signal. The method may utilize a high speed optical chopper configured to periodically interrupt the laser light beam between the laser light source and the sample; and using the high speed optical chopper to provide a synchronized time-gated optical window for receiving mostly Raman signal while rejecting most or some of the fluorescence signal transmitted from the sample in response to the laser light beam before reaching the sensor.

15 Claims, 8 Drawing Sheets

(51) Int. Cl.
  *G01N 21/65* (2006.01)
  *G02B 21/16* (2006.01)
  *G02B 26/04* (2006.01)
(52) U.S. Cl.
  CPC ............ *G01J 3/4412* (2013.01); *G01N 21/65* (2013.01); *G02B 21/16* (2013.01); *G02B 26/04* (2013.01); *G01N 2201/06113* (2013.01)

(56) References Cited

U.S. PATENT DOCUMENTS

| | | |
|---|---|---|
| 4,505,586 A | 3/1985 | Tochigi et al. |
| 5,141,312 A * | 8/1992 | Thompson ................. G01J 1/04 250/227.11 |
| 5,545,517 A * | 8/1996 | Thompson ............. C12Q 1/527 356/301 |
| 6,061,134 A | 5/2000 | Jensen et al. |
| 6,621,574 B1 * | 9/2003 | Forney ..................... G01J 3/02 250/252.1 |
| 6,937,331 B1 * | 8/2005 | Nguyen ................ G01J 3/2823 356/305 |
| 2011/0022328 A1 * | 1/2011 | Granot ................. G01N 21/359 702/19 |

OTHER PUBLICATIONS

International Search Report based on application No. PCT/SG2014/000501 (4 pages) dated Dec. 22, 2014 (for reference purpose only).

* cited by examiner

RAMAN SPECTROSCOPY SYSTEMS AND RAMAN SPECTROSCOPY METHODS

RELATED APPLICATIONS

The present application is a national stage entry according to 35 U.S.C. § 371 of PCT application No.: PCT/SG2014/000501 filed on Oct. 24, 2014, and is incorporated herein by reference in its entirety.

TECHNICAL FIELD

Embodiments relate generally to Raman spectroscopy systems and Raman spectroscopy methods.

BACKGROUND

Raman spectroscopy is an analytical technique that probes into the vibrational properties of the material. It has broad applications range in both research and industrial settings for analyzing solid, liquid and gases. In this technique, a monochromatic light source such as a laser is directed toward a test sample and inelastic scattering of photons from molecules which provides information about the molecular composition and may yield a fingerprint of the constituent molecules are observed. An advantage of this technique is that no sample preparation is required and observation can be relatively quick, ranging from ms (milliseconds) to tens of seconds.

However, some measurements of Raman signal are often masked by a strong background fluorescence coming from the sample such as biological tissues, organic substances, pharmaceutical drugs, etc. The fluorescence may be so overwhelming that no Raman peaks can be observed, making it difficult for material identification and concentration measurement applications. Thus, there is a need for devices and methods which reduce background fluorescence in Raman spectroscopy.

SUMMARY

According to various embodiments, a Raman spectroscopy system may be provided. The Raman spectroscopy system may include: a laser light source configured to provide a laser light beam directed to a sample; an optical chopper configured to periodically interrupt the light beam between the laser light source and the sample; and a sensor configured to receive signal light transmitted from the sample in response to the light beam.

According to various embodiments, a Raman spectroscopy method may be provided. The Raman spectroscopy method may include: providing a laser light beam from a laser light source directed to a sample; periodically interrupting the light beam between the laser light source and the sample; and receiving signal light transmitted from the sample in response to the light beam.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Embodiments described below in context of the devices are analogously valid for the respective methods, and vice versa. Furthermore, it will be understood that the embodiments described below may be combined, for example, a part of one embodiment may be combined with a part of another embodiment.

Raman spectroscopy is an analytical technique that probes into the vibrational properties of the material. It has broad range applications in both research and industrial settings for analyzing solid, liquid and gases. In this technique, a monochromatic light source such as a laser is directed toward a test sample and inelastic scattering of photons from molecules via interactions with the vibrational modes within the molecule are observed. The interaction of light with molecule will induce a change in the polarizability of the molecule. The interaction of the polarizability with the incoming radiation results in induced dipole moment in the molecule. The light scattered from the induced dipole consist of both Rayleigh and inelastic (Raman) scatterings. Rayleigh scattering corresponds to the light scattered at the wavelength of the incoming radiation. Raman scattering is wavelength-shifted from the incoming radiation wavelength by the vibrational energy that is either gain or loss in a molecule. It is this wavelength shift of the inelastically scattered radiation which yields the chemical and structural information of the molecule. The advantages of this technique is that no sample preparation is required, no interference by water, non-destructive and observation can be relatively quick, ranging from ms (milliseconds) to tens of seconds.

However, some measurements of Raman signal may be often masked by a strong background fluorescence coming from the sample such as biological tissues, organic substances, pharmaceutical drugs, etc. The fluorescence can be so overwhelming that no Raman peaks can be observed, making it difficult for material identification and concentration measurement applications.

Figure 1:
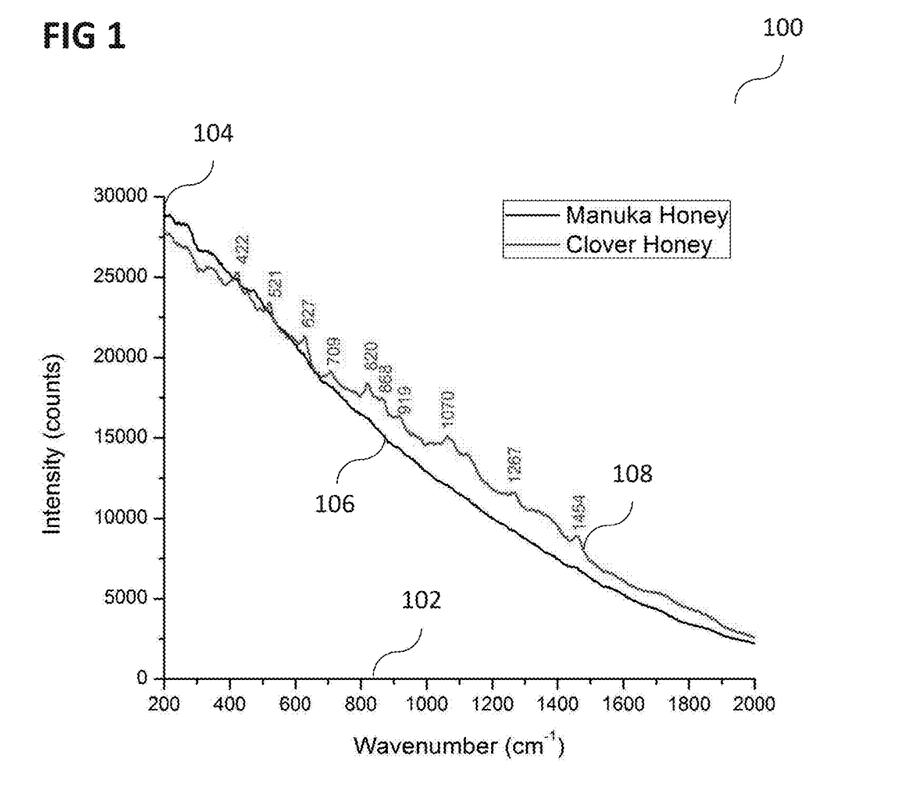
FIG. 1 shows an illustration of Raman spectra of commercial honey both containing high level of background fluorescence.

FIG. 1 shows an illustration 100 of Raman spectra of commercial honey both containing high level of background fluorescence. A horizontal axis 102 denotes the Raman shift, and a vertical axis 104 denotes the intensity. A plot 106 is shown for manuka honey, and a plot 108 is shown for clover honey. The major portion of honey consists of monosaccharides fructose and glucose. Referring to Raman spectrum of clover honey, plot 108, the Raman peaks at 422, 627, 709, 820 and 868 $cm^{-1}$ constitute to fructose, whereas. Raman peaks at 521, 919, 1070, 1267 and 1454 $cm^{-1}$ constitute to both fructose and glucose. However strong fluorescence will overwhelm the Raman peaks, making it difficult for analysis.

This is worst for Raman spectrum obtained from manuka honey in which no Raman peaks can be visible. To reduce fluorescence, most work involved diluting the concentrated honey prior to spectrum acquisition. This creates additional preparation steps as well as reduction in signal.

Various approaches may address this problem, like will be described in the following.

In one approach, fluorescence may be effectively suppressed by using near-infrared laser operating at 1064 nm instead of traditional short laser wavelengths from Ultra-violet (UV) to Near Infra-Red (NIR) such as 350 nm to 830 nm. However, this method presents some shortfalls. Using 1064 nm laser requires the use of InGaAs (Indium gallium arsenide) or Ge (Germanium) CCD (Charge-coupled Device) detectors which may have noise that is several orders of magnitude higher than the conventional silicon CCD that is used with shorter wavelength lasers. A further shortfall may be that the Raman scattering intensity may be inversely proportional to the excitation laser wavelength to the power of four. For example, a 785 nm laser has 3.4 times more scattering intensity than using a 1064 nm laser. Hence, to overcome these above mentioned issues, a need for higher excitation laser power (>1000 mW vs 10s mW to 100s mW with shorter wavelength laser) and longer integration time may arise.

Another approach may involve a time-resolved technique, like will be described in the following.

Figure 2:
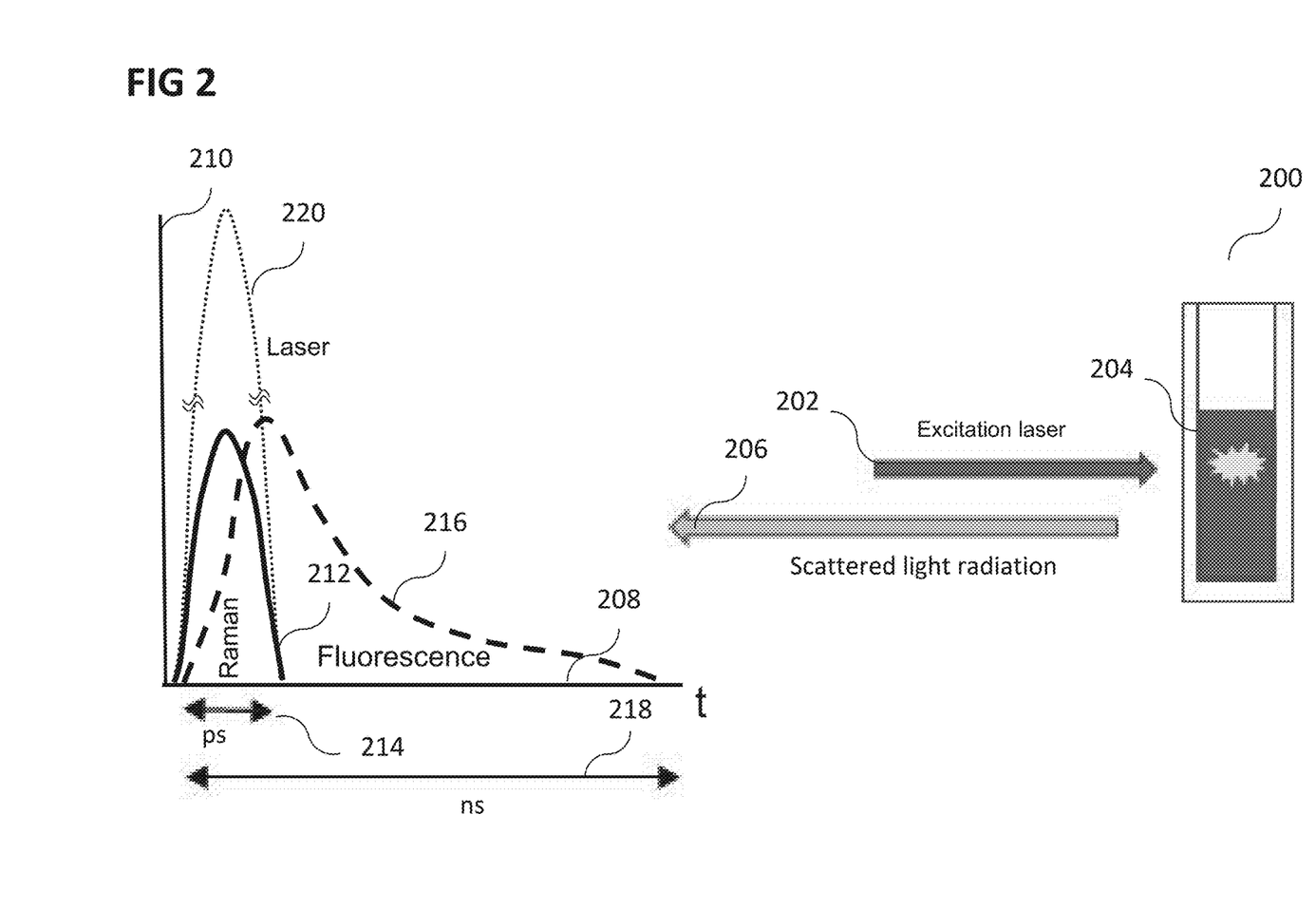
FIG. 2 shows a schematic diagram of the timescale of Raman and fluorescence signals.

FIG. 2 shows a schematic diagram 200 of the timescale of Raman and fluorescence signals. On the right hand side of FIG. 2, a sample 204 under investigation is shown, which is excited by an excitation laser 202, and which emits scattered light radiation 206 in response to the excitation by excitation laser 202. The left hand side of FIG. 2 shows a graph of an intensity 210 over time 208 of Raman light 212 and fluorescence light 216. In terms of time scale, Raman scattering occurs immediately with laser excitation in the region of femtosecond or less (like indicated by arrow 214) whereas fluorescence has a lifetimes that are typically in the order of nanoseconds (like indicated by arrow 218. Hence it may be possible to suppress fluorescence background to a great extend if the sample is illuminated with short laser pulses (for example ps (picosecond) to tens of ns (nanosecond)) rather than continuous wave laser and collecting the signal within the same pulse duration period, thereby generating lesser fluorescence. The Raman signal occurs instantaneously and had been measured to femtosecond (limited by measuring instruments). However, it occurs together with the laser; thus the picosecond mentioned in FIG. 2 is the pulse duration of the Laser where the shortest pulsed laser used for Raman are in their picosecond, hence it is to be noted that the Raman signal mirrors the laser pulse in timing.

Techniques of reducing sample background fluorescence may employ time-gate technique with ultrafast laser and high speed camera, avalanche photodetector array or photomultiplier tube (PMT) to separate the Raman signal from the fluorescence. In this technique, when a short-pulsed laser is used to excite the sample of interest, a trigger signal will be sent to the camera, detector array or PMT to time its collection of the scattered signal from the sample. As the Raman scattered and fluorescence emission occurs in separate time frames when excited by short-pulsed lasers, collection of the fluorescence emission can be minimized by timing the collection time of the detectors to match only the time of Raman scattering. While this time-resolved technique may be able to separate Raman signal from background fluorescence, it may require sophisticated equipment and setup. In additional, the cost involved may be very high thus making it impractical for portable applications and most industrial companies.

According to various embodiments, devices and methods may be provided to reduce background fluorescence by using a high speed optical spin-disk (HSOSD), or optical chopper in general, approach to create time-gated short pulses and collection in a Raman spectroscopy measurement. According to various embodiments, the high speed optical spin-disk system may be integrated with any standard Raman spectroscopy setup and thus will reduce the setup complexity. No ultrashort pulse lasers and expensive high speed sensor may be required in the setup, but regular continuous wave laser and sensor array may be used and hence the device and methods according to various embodiments may provide a simple and low cost solution.

According to various embodiments, devices and methods may be provided which reduce background fluorescence in Raman spectroscopy.

Figure 3A:
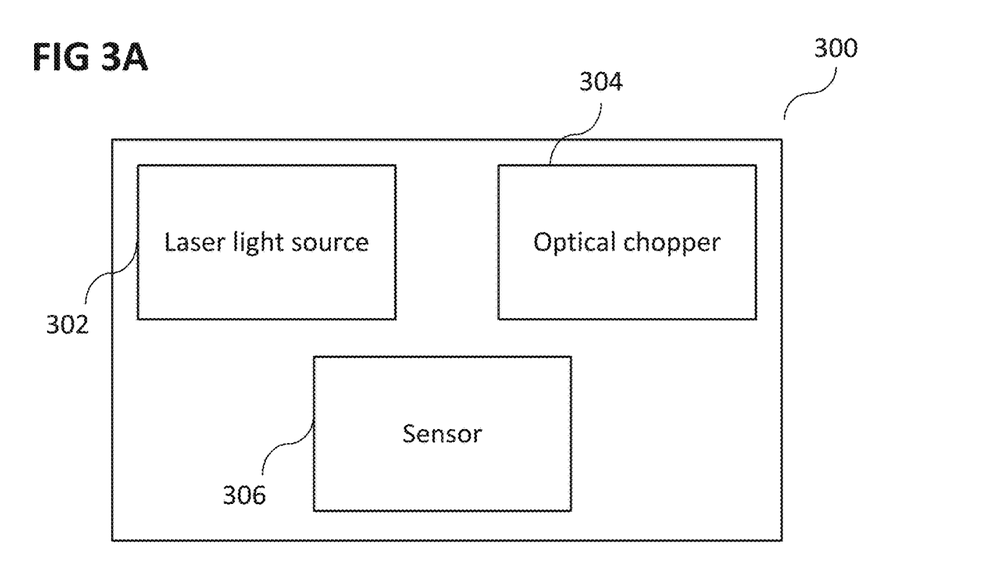
FIGS. 3A and 3B show Raman spectroscopy systems according to various embodiments.

FIG. 3A shows a Raman spectroscopy system 300 according to various embodiments. The Raman spectroscopy system 300 may include a laser light source 302 configured to provide a (for example continuous; in other words: uninterrupted) laser light beam directed to a sample (not shown in FIG. 3A). The Raman spectroscopy system 300 may further include an optical chopper (in general) or a High Speed Optical Spin disk (HSOSD) 304 configured to periodically interrupt the light beam between the laser light source 302 and the sample. The Raman spectroscopy system 300 may further include a sensor 306 configured to receive light signal transmitted from the sample in response to the laser light beam (for example shattered or emitted from the sample after being hit by the laser light beam).

In other words, according to various embodiments, a Raman spectroscopy system may be provided in which a continuous laser light beam, directed to a sample, is modulated (in other words: periodically interrupted), so that effectively, laser light impinges on the sample only for a short period of time, before being interrupted. In additional, the signal will, after being collected by the focusing optics, return through the same or offset optical path as the excitation laser and pass through the small optical windows on the optical chopper disk. The optical chopper disk will act as a time-limited windows allowing mostly Raman signal to pass and block most or some of the fluorescence signal.

According to various embodiments, the disk may include a plurality of clear windows (in other words: windows which the laser light beam and the signal light beam may pass) and a plurality of laser light blocking windows (in other words: windows which the laser light beam may not pass; in other words: windows which may block the laser light beam and the returning signal light beam).

According to various embodiments, the plurality of clear windows and the plurality of laser light blocking windows may be arranged mostly on the outer part of the disk or throughout the disk for different timing arrangement.

FIG. 3A shows a Raman spectroscopy system 300 according to various embodiments. The Raman spectroscopy system 300 may include a laser light source 302 configured to provide a (for example continuous; in other words: uninterrupted) laser light beam directed to a sample (not shown in FIG. 3A). The Raman spectroscopy system 300 may further include an optical chopper 304 configured to periodically interrupt the laser light beam between the laser light source and the sample. The Raman spectroscopy system 300 may further include a sensor 306 configured to receive signal light transmitted from the sample in response to the laser light beam (for example shattered from the sample after being hit by the laser light beam).

In other words, according to various embodiments, a Raman spectroscopy system may be provided in which a continuous laser light beam, directed to a sample, is chopped (in other words: periodically interrupted; in other words: modulated), so that effectively, laser light impinges on the sample only for a short period of time, before being interrupted. The period of time may be chosen to be long enough for Raman light to be emitted (in other words: scattered) from the sample, but to be short enough so that no (or only a small amount of) fluorescent light is received at the sensor from the sample (for example fluorescent light may be blocked by the optical chopper after a short period of time).

According to various embodiments, the optical chopper 304 may further be configured to periodically interrupt the signal light from the sample between the sample and the laser light source 302.

According to various embodiments, the optical chopper 304 may include or may be or may be included in a disk, wherein the disk may be configured to rotate.

According to various embodiments, the disk may include a plurality of clear windows and a plurality of laser light blocking windows.

According to various embodiments, the plurality of laser light blocking windows may further be configured to block the signal light.

According to various embodiments, the plurality of clear windows and the plurality of laser light blocking windows may be arranged throughout the disk.

According to various embodiments, the optical chopper 304 may be configured to provide a modulating of the laser light beam before it reaches the sample.

According to various embodiments, the same optical chopper may be used to provide a time-gated window for the signal light before it reaches the sensor.

According to various embodiments, a different optical chopper may be used to provide a time-gated window for the signal light before it reaches the sensor.

According to various embodiments, the sensor 306 may include or may be included in a spectrometer with linear detector array or area detector array.

Figure 3B:
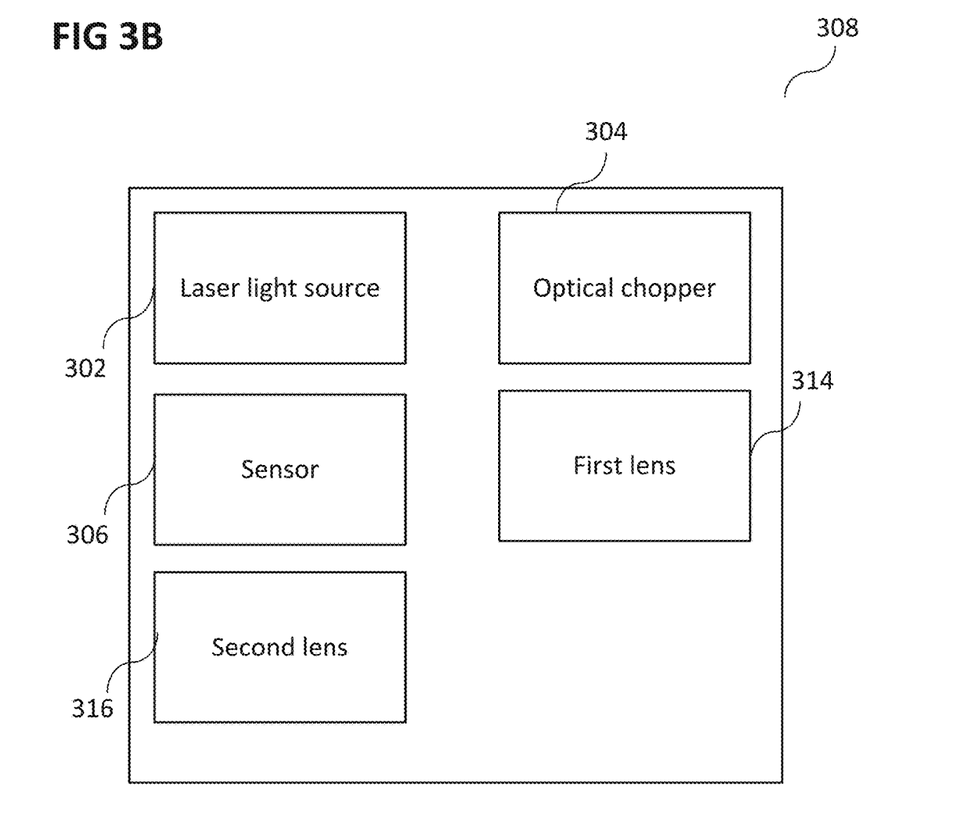

FIG. 3B shows a Raman spectroscopy system 308 according to various embodiments. The Raman spectroscopy system 308 may, similar to the Raman spectroscopy system 300 of FIG. 3A, include a laser light source 302 configured to provide a (for example continuous; in other words: uninterrupted) laser light beam directed to a sample (not shown in FIG. 3A). The Raman spectroscopy system 308 may, similar to the Raman spectroscopy system 300 of FIG. 3A, further include an optical chopper 304 configured to periodically interrupt the laser light beam between the laser light source and the sample. The Raman spectroscopy system 308 may, similar to the Raman spectroscopy system 300 of FIG. 3A, further include a sensor 306 configured to receive signal light transmitted from the sample in response to the laser light beam (for example shattered from the sample after being hit by the laser light beam). The Raman spectroscopy system 308 may further include a first lens 314, like will be described below. The Raman spectroscopy system 308 may further include a second lens 316, like will be described below.

According to various embodiments, the first lens 314 may be configured to focus the laser light beam to the optical chopper.

According to various embodiments, the second lens 316 may be configured to collimate the laser light beam from the optical chopper.

Figure 3C:
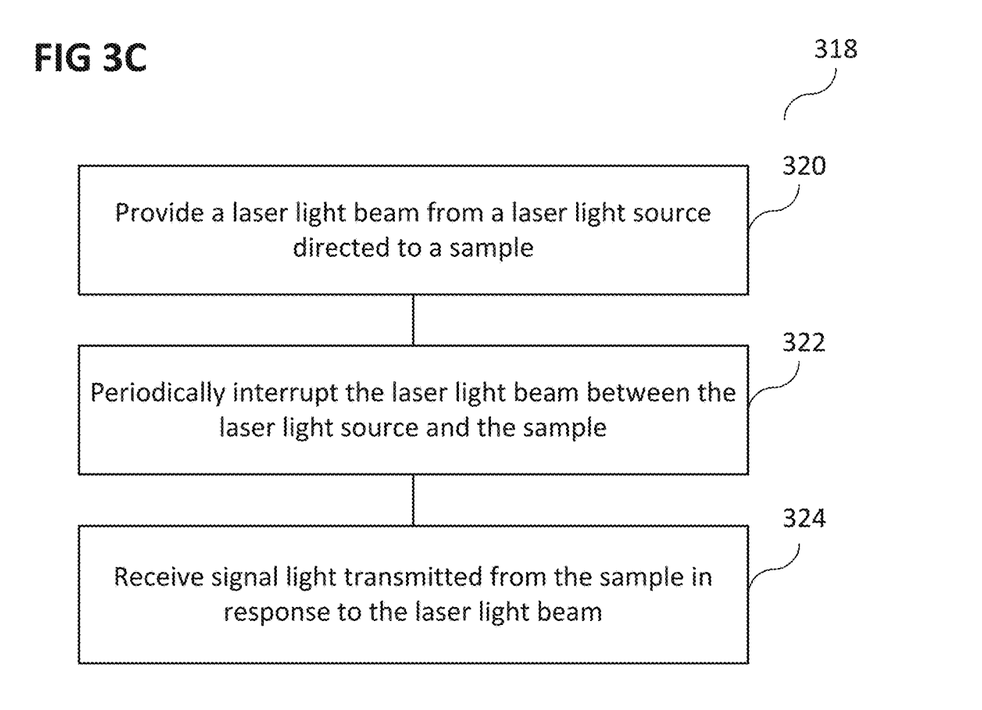
FIG. 3C shows a flow diagram illustrating a Raman spectroscopy method according to various embodiments.

FIG. 3C shows a flow diagram 318 illustrating a Raman spectroscopy method according to various embodiments. In 320, a laser light beam may be provided from a laser light source directed to a sample. In 322, the laser light beam between the laser light source and the sample may be periodically interrupted. In 324, signal light transmitted from the sample in response to the laser light beam may be received (for example in a sensor).

According to various embodiments, the method may further include periodically interrupting the signal light from the sample between the sample and the laser light source.

According to various embodiments, the optical chopper, in general, or High Speed Optical Spin Disk (HSOSD) may include or may consist of single digit micro-meter (or of any size) clear windows with rectangular, square, round, hexagonal or any shapes, and single digit micro-meter (or of any size) blocking windows arranged throughout (for different timing arrangement) or mostly on the outer part of the disk. The clear windows may be uncoated part of the disk, or through holes; while the blocking windows may be coated with reflective or opaque material or may be just the uncut part of the slotted disk.

According to various embodiments, the optical chopper, in general, or High Speed Optical Spin Disk (HSOSD) may be rotated or spin or provide modulation in the range of 100s of kilohertz to 10s of megahertz (or any speed faster than 10s of kilohertz).

Figure 4A:
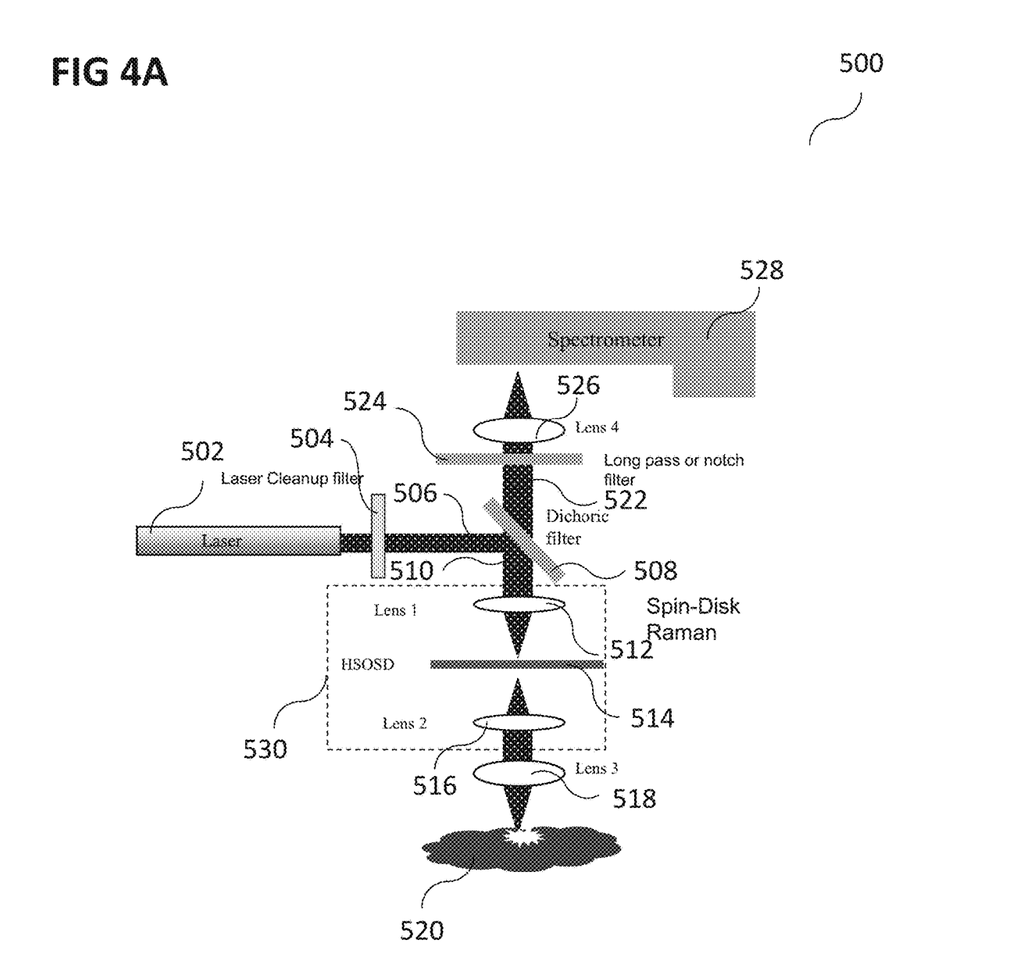
FIG. 4A, FIG. 4B, and FIG. 4C show schematic diagrams of a Raman spectroscopy system setup with the inclusion of a high speed optical spin disk (HSOSD) or optical chopper (in general) according to various embodiments.
Figure 4B:
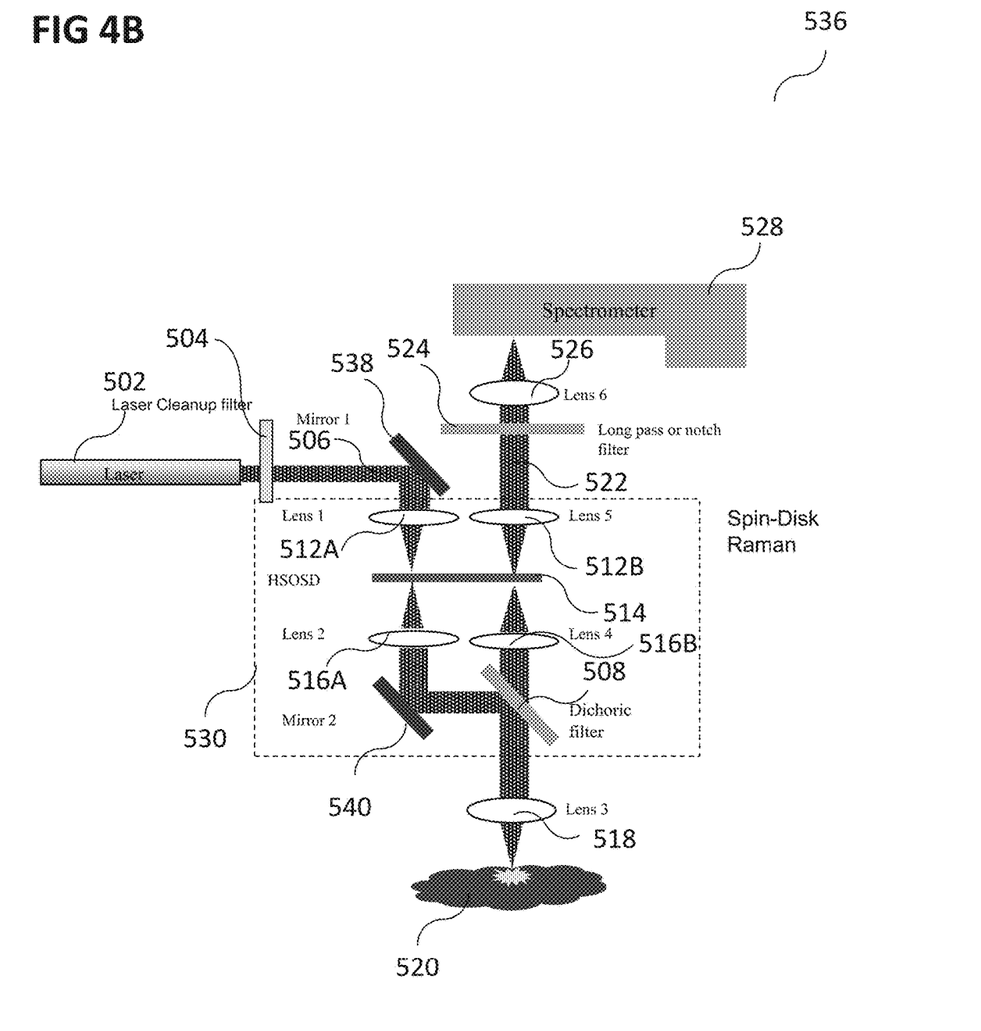
Figure 4C:
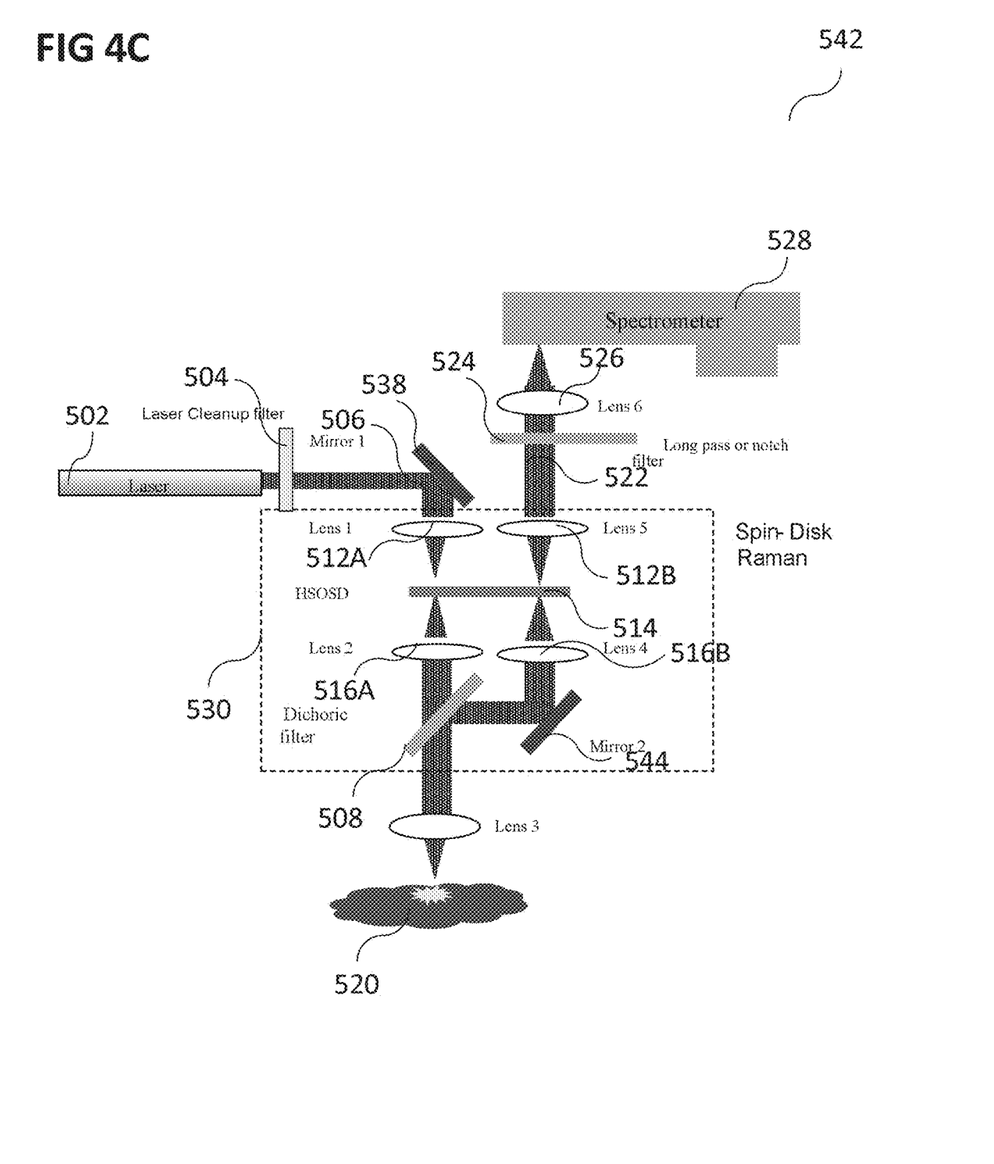

FIGS. 4A, 4B and 4C show schematic diagrams 500, 536, and 542 (in other words: schematic layouts) of Raman spectroscopy system setups with the inclusion of the HSOSD 514 (which may also be referred to as an optical chopper) according to various embodiments.

Light of an excitation laser 502 (which may for example emit light of a wavelength ranging from 200 nm to 830 nm, or any singular or multiple wavelength), after passing through a laser cleanup filter 504 (like indicated by light path 506), may be redirected by a dichroic filter 508 (or notch filter or optical device), like indicated by light path 510 and may be focused to a small spot by a first lens 512. A second lens 516 may expand and re-collimate the laser into the back aperture of an objective lens 518 (which may be referred to as a third lens). The third lens 518 may then focus the light onto the sample 520 (for example directly, like shown in FIG. 4A) of interest or the proximal end of an optical fiber probe. The third lens 518 may also collect the back scattered Raman signal from the sample 520. The back scattered Raman signal may follow the excitation laser path (or with offset) back to the dichroic filter 508, passing the HSOSD 514. As Raman scattering is instantaneous as compared to fluorescence, the back scattering Raman signal may be aligned to pass through the same or different HSOSD 514 clear window slit as the excitation light. Most or some of the fluorescence signal, which has a longer lifetime than the Raman signal, may miss the clear windows slit and may be blocked by the opaque slit on the HSOSD 514. The first lens 512, the HSOSD 514, and the second lens 516 may also be referred to as "spin-disk Raman" system 530. As shown in FIGS. 4B and 4C, further mirrors (538 and 540 in FIG. 4B, or 538 and 544 in FIG. 4C) may be provided, and separate pairs of lenses (a first pair 512A, 516A and a second pair 512B, 516B) may be provided for focusing the laser light to the HSOSD 514 and focusing the signal light to the HSOSD.

Since the back scatter Raman signal is of longer or shorter wavelength than the excitation laser the Raman signal may pass through the dichoric filter or optical beam splitter (like indicated by light path 522) and a long pass filter 524 (or notch filter or short pass filter) before being focused into a spectrometer 528 for analysis via a fourth lens 526.

Figure 5:
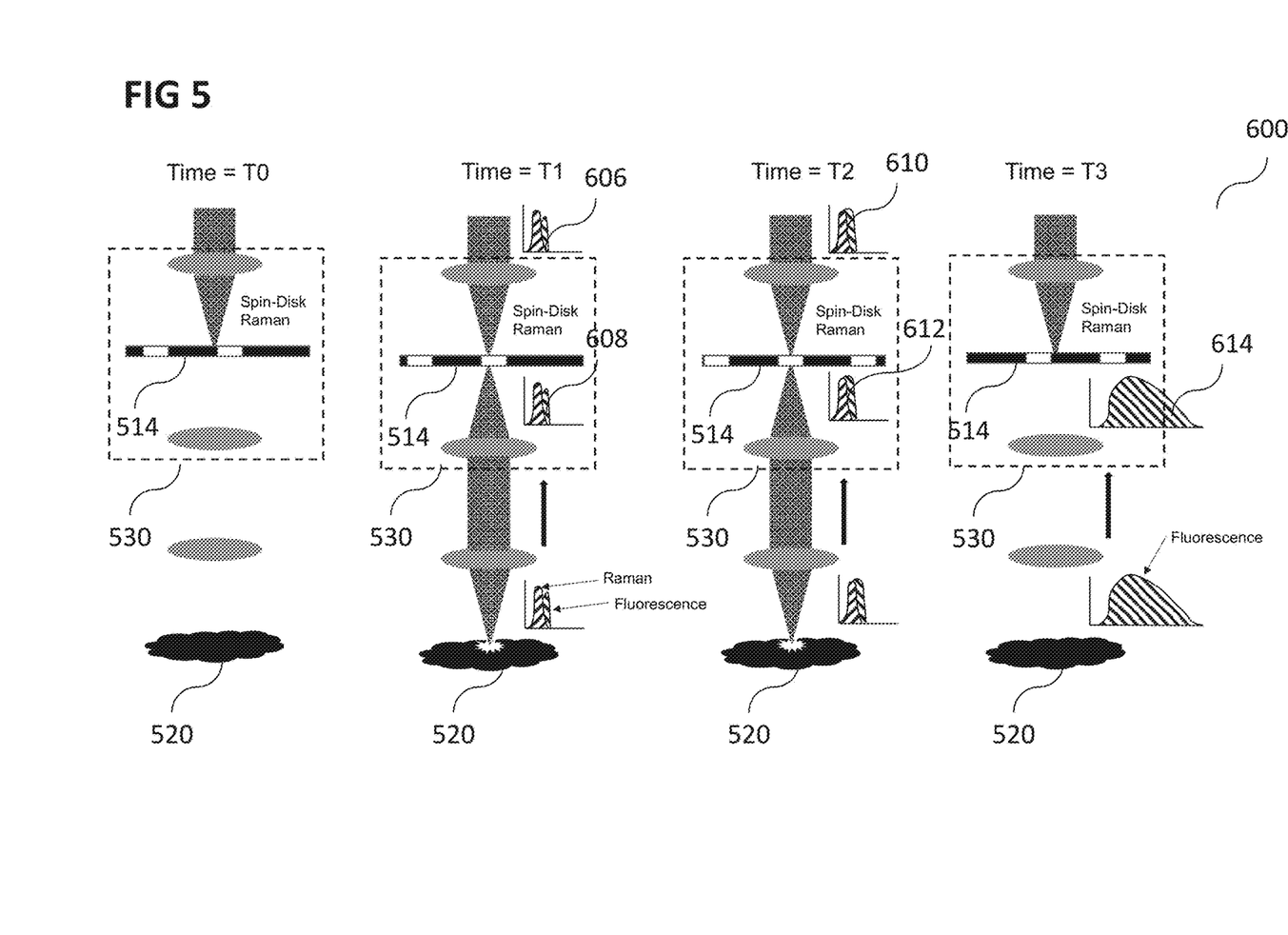
FIG. 5 shows and illustration 600 of a portion of the spin-disk Raman system at various points in time.

FIG. 5 shows and illustration 600 of a portion of the spin-disk Raman system at various points in time. At a first point of time T0, the HSOSD 514 does not let pass laser light to the sample 520. At a second point of time T1 and a third point of time T2, the HSOSD 514 lets pass laser light to the sample 520 and also lets pass signal light from the sample 520 to the sensor (like indicated in graphs 608 and 606 for T1, and 612 and 610 for T2). As illustrated, the amount of fluorescence increases over time as it accumulates with its longer lifetime compare to Raman. At a fourth point of time, fluorescence may be so high, that the Raman light may not be detected, but may be covered by the fluorescence light (like shown in graph 614). At this point of time, the HSOSD 514 has already rotated further, so as to block the fluorescence light. As such, according to various embodiments, the HSOSD may be used to time-gate the signal collection with respect to the excitation laser and block most or some of the overwhelming fluorescence signal allowing mainly Raman light to be received by the detector.

A high speed optical spin disk with multiple small width windows slits according to various embodiments may facilitate small pulse width laser with a continuous laser that may be used to excite samples. Due to the short time duration of the same clear window slit, which is passed by the excitation laser, mostly Raman signal will be able to pass through it.

According to various embodiments, a Raman spectroscopy method is provided for reduction of background fluorescence signal. The method may utilize a high speed optical chopper configured to periodically interrupt the laser light beam between the laser light source and the sample; and using the high speed optical chopper to provide a synchronized time-gated optical window for receiving mostly Raman signal while rejecting most or some of the fluorescence signal transmitted from the sample in response to the laser light beam before reaching the sensor.

According to various embodiments, an optical chopper configured to periodically interrupt the light beam path between the laser light source and the sample may be provided.

According to various embodiments, a method for time-resolved Raman spectroscopy for fluorescence removal may be provided, in which an optical chopper or spin disk is utilized as a time gated frequency modulator for laser excitation and signal light collection, and for time gating the laser excitation and signal collection in Raman Spectroscopy for Fluorescence background removal or reduction.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A Raman spectroscopy system for measuring Raman signal of a sample exhibiting Raman and fluorescence, the system comprising:
   a laser light source configured to provide a laser light beam directed to a sample in order to obtain a signal light scattered from the sample comprising a Raman component and a fluorescence component;
   an optical chopper configured to periodically interrupt the laser light beam between the laser light source and the sample, and
   wherein the optical chopper is further configured to periodically interrupt the signal light from the sample between the sample; and
   a sensor configured to receive a non-interrupted portion of the signal light, wherein the non-interrupted portion of the signal light comprises a main portion of the Raman signal component and the interrupted portion of the signal light immediately following the non-interrupted portion comprises at least a portion of the fluorescence component;
   wherein the optical chopper comprises a disk, and wherein the optical chopper provides modulation at least at 1 megahertz.

2. The Raman spectroscopy system of claim 1, wherein the disk comprises a plurality of clear windows and a plurality of laser light blocking windows.

3. The Raman spectroscopy system of claim 2, wherein the plurality of laser light blocking windows are further configured to block the signal light.

4. The Raman spectroscopy system of claim 3, wherein the laser light beam comprises a laser light beam path and the signal light comprises a signal light path, and wherein the laser light beam path and the signal light path intersect at a same modulation position in which they are further intersecteable by the plurality of laser light blocking windows.

5. The Raman spectroscopy system of claim 2, wherein the plurality of clear windows and the plurality of laser light blocking windows are arranged at the outer part of or throughout the disk.

6. The Raman spectroscopy system of claim 2, wherein a plurality of clear windows are of 10 micrometer or smaller in width.

7. The Raman spectroscopy system of claim 1, wherein the optical chopper is used to provide a synchronized time-gated window for the signal light before it reaches the sensor, for reducing background fluorescence component.

8. The Raman spectroscopy system of claim 1, wherein a different part of the same optical chopper is used to provide a time-gated window for the signal light before it reaches the sensor.

9. The Raman spectroscopy system of claim 1, wherein the sensor comprises a spectrometer with linear detector array or area detector array.

10. The Raman spectroscopy system of claim 1, further comprising:
    a first lens configured to focus the laser light beam to the optical chopper.

11. The Raman spectroscopy system of claim 1, further comprising:
    a second lens configured to re-collimate the laser light beam from the optical chopper.

12. The Raman spectroscopy system of claim 1, wherein the laser light source is a continuous wave laser.

13. The Raman spectroscopy system of claim 1, wherein the optical chopper is configured to provide a synchronized time-gated optical window for laser excitation and signal light collection through the same time-gated optical window.

14. A Raman spectroscopy method for measuring Raman signal of a sample exhibiting Raman and fluorescence, the method comprising:

providing a laser light beam from a laser light source directed to a sample in order to obtain a signal light scattered from the sample comprising a Raman component and a fluorescence component;

periodically interrupting the laser light beam between the laser light source and the sample with an optical chopper;

and periodically interrupting the signal light from the sample between the sample and the laser light source with the optical chopper, and receiving a non-interrupted portion of the signal light, wherein the non-interrupted portion of the signal light comprises a main portion of the Raman signal component and the interrupted portion of the signal light immediately following the non-interrupted portion comprises at least a portion of the fluorescence component;

wherein the optical chopper comprises a disk and provides modulation at least at 1 megahertz.

15. The Raman spectroscopy method of claim 14, wherein the laser light source is a continuous wave laser.

* * * * *